(12) United States Patent
Lin et al.

(10) Patent No.: US 7,614,275 B2
(45) Date of Patent: Nov. 10, 2009

(54) METHOD AND APPARATUS FOR DETERMINING COEFFICIENT OF FRICTION

(75) Inventors: Cheng-Hsiung Lin, Hudson, OH (US); Joel Joseph Lazeration, Copley, OH (US)

(73) Assignee: The Goodyear Tire and Rubber Company, Akron, OH (US)

( * ) Notice: Subject to any disclaimer, the term of this patent is extended or adjusted under 35 U.S.C. 154(b) by 287 days.

(21) Appl. No.: 11/684,217

(22) Filed: Mar. 9, 2007

(65) Prior Publication Data

US 2008/0156067 A1 Jul. 3, 2008

Related U.S. Application Data

(60) Provisional application No. 60/882,647, filed on Dec. 29, 2006.

(51) Int. Cl.
*G01N 3/56* (2006.01)

(52) U.S. Cl. .......................................................... 73/9

(58) Field of Classification Search .................... 73/7–9
See application file for complete search history.

(56) References Cited

U.S. PATENT DOCUMENTS

| | | | |
|---|---|---|---|
| 3,563,135 A * | 2/1971 | Trader et al. .................. 91/385 |
| 3,640,118 A * | 2/1972 | Geis ................................... 73/9 |
| 5,113,688 A | 5/1992 | Lazeration |
| 5,814,718 A * | 9/1998 | Andresen et al. .................. 73/9 |
| 5,864,056 A * | 1/1999 | Bell et al. ...................... 73/146 |
| 5,892,139 A * | 4/1999 | Miyazaki .......................... 73/9 |
| 5,900,531 A | 5/1999 | Mani et al. |
| 6,199,424 B1 | 3/2001 | Mani et al. |
| 6,349,587 B1 | 2/2002 | Mani et al. |
| 6,489,389 B1 | 12/2002 | Ohta et al. |
| 6,550,508 B1 | 4/2003 | Yamaguchi et al. |
| 2002/0169245 A1 | 11/2002 | Ohta et al. |
| 2005/0032960 A1 | 2/2005 | Kishimoto et al. |

\* cited by examiner

*Primary Examiner*—Hezron Williams
*Assistant Examiner*—Alex Devito
(74) *Attorney, Agent, or Firm*—Roger D. Emerson; Daniel A. Thomson; Emerson, Thomson and Bennett

(57) ABSTRACT

The coefficient of friction of an elastomeric sample can be determined by: (a) providing a friction test machine having a rigid wheel with an outer surface defining a curvilinear friction surface, a sample holder and, a force measurement device; (b) placing the elastomeric sample onto the sample holder; (c) adjusting the elastomeric sample and the curvilinear friction surface into frictional engagement thereby forming a curvilinear deformation in the elastomeric sample; (d) rotating the rigid wheel; and, (e) using the force measurement device to obtain a geometry independent measurement indicative of the coefficient of friction of the elastomeric sample.

19 Claims, 16 Drawing Sheets

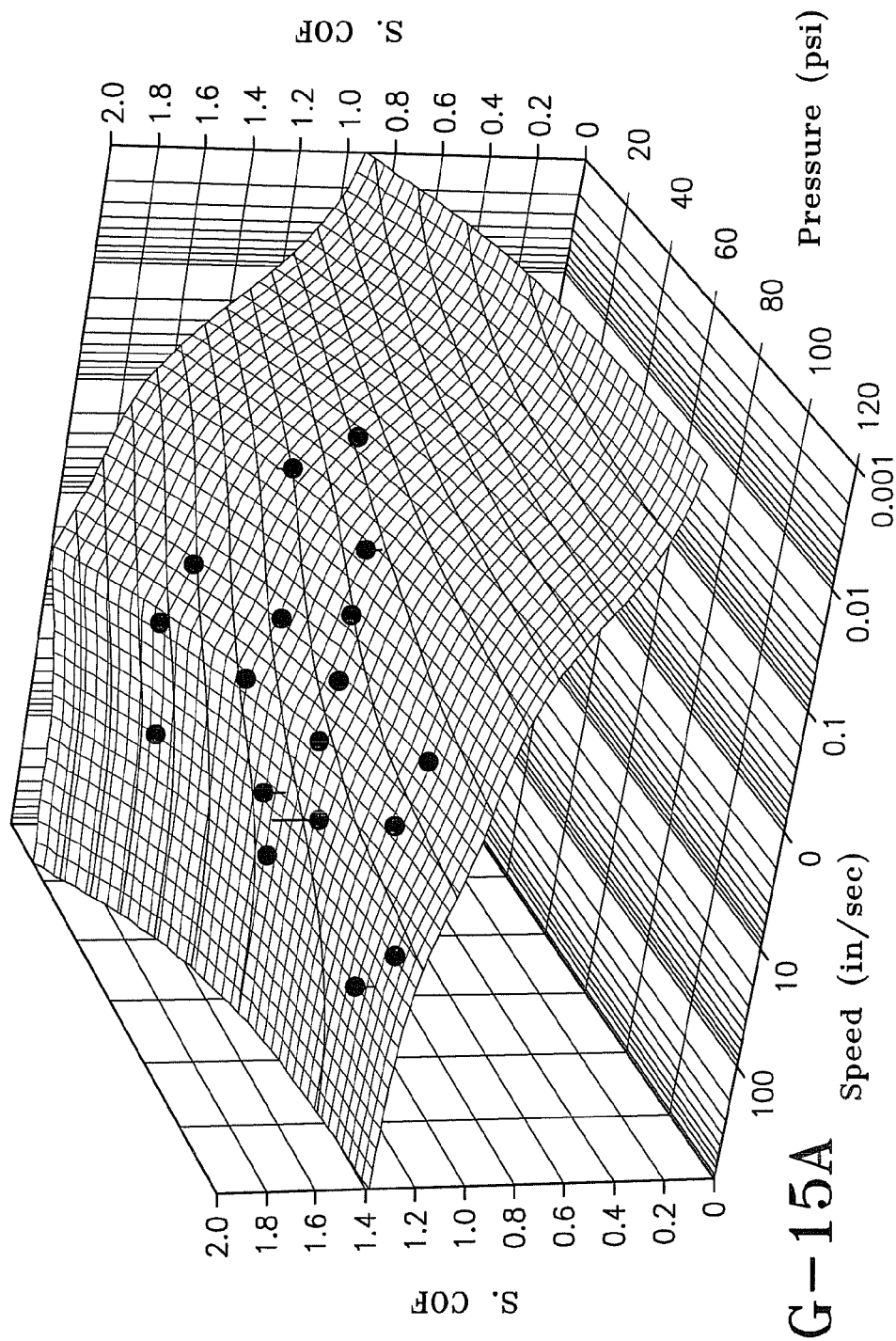

METHOD AND APPARATUS FOR DETERMINING COEFFICIENT OF FRICTION

This application claims priority to U.S. Ser. No. 60/882,647, entitled METHOD AND APPARATUS FOR DETERMINING COEFFICIENT OF FRICTION, filed Dec. 29, 2006, which is incorporated herein by reference.

I. BACKGROUND OF THE INVENTION

A. Field of Invention

This invention pertains to the art of methods and apparatuses regarding the determination of the coefficient of friction of a composition, especially an elastomeric material such as the tread of an existing tire.

B. Description of the Related Art

Coefficient of friction is an intrinsic property of a material and the substrate it is touching. Therefore, its value should be geometry independent. In practice, however, this is typically not the case. It is well know, for example, to determine the "coefficient of friction" of a tire tread in a manner where the geometry of the tread blocks and tread sipes within the blocks affect the result. It would be more accurate to refer this property as "coefficient of traction" because sample geometry is a contributing factor.

It is desirable to describe coefficient of friction in terms of contact stress (pressure), sliding velocity or strain rate, temperature, humidity, substrate properties, etc. With reference to FIG. 1, conventional tests for coefficient of friction often use a block specimen 1 where the specimen's geometry contributes to the frictional force (Fxy) developed between the specimen 1 and the substrate 2. This is due to mechanical interference between the leading edge 3 of the block 1 and the substrate 2 and the non-uniform distribution of contact stresses at the interface. A phenomenon known as "frictional lift" often occurs as the trailing edge 4 of the block 1 loses contact with the substrate 2 because of the couple induced in the specimen 1. These problems at the leading edge 3 and the trailing edge 4 of the specimen 1 are, in this patent, referred to individually and collectively as "edge effects." The goal for the measurement of coefficient of friction is therefore to minimize geometric effects so as to best approximate the true point-wise value U.S. Pat. No. 6,349,587, titled PORTABLE UNIVERSAL FRICTION TESTING MACHINE AND METHOD (the '587 patent) is an example of a conventional friction testing machine used with tire compounds. This machine is said to measure the coefficient of friction between a rubber specimen and a friction surface. It should be pointed out, however, that the friction testing machine of the '587 patent as well as most of those known in the prior art do not account for the specific geometry of the test samples and thereby edge effects distort the true friction characteristics.

U.S. Pat. No. 5,113,688, titled LABORATORY TRACTION TEST (the '688 patent) has a common assignee and is incorporated herein by reference. The '688 patent discloses an apparatus, called a Rotational Friction Tester (RFT), that predicts tire traction characteristics by measuring the friction characteristics of the samples. The specific geometry of the samples, shown in FIG. 3B of the '688 patent, eliminates the edge effects to better isolate the actual friction characteristics of the sample. These samples, however, must be carefully formed and cured into this particular shape in order to remove the edge effects. As a result, it is not possible to find accurate friction characteristics of samples from existing tires or other products where the specific composition of the product is unknown.

This invention solves these problems by providing a friction testing apparatus and method that eliminates edge effects and provides accurate coefficient of friction measurements for samples independent of the specific sample geometry.

II. SUMMARY OF THE INVENTION

According to one embodiment of this invention, a friction test machine may include: (a) a frame; (b) a curvilinear friction surface; (c) a rotation device configured to selectively rotate the curvilinear friction surface; (d) a sample holder configured to hold a sample; (e) a motion device configured to selectively adjust the sample and the curvilinear friction surface into frictional engagement; and, (f) a force measurement device for obtaining a measurement indicative of the coefficient of friction of the sample.

According to another embodiment of this invention, the outer surface of a wheel defines the curvilinear friction surface and the rotation device is configured to selectively rotate the wheel.

According to another embodiment of this invention, the force measurement device is configured to obtain a measurement indicative of the coefficient of friction of an elastomeric sample.

According to still another embodiment of this invention, the force measurement device is configured to obtain a measurement indicative of the coefficient of friction of an actual tire tread sample.

According to another embodiment of this invention, the force measurement device is configured to obtain a measurement indicative of both static and kinetic coefficient of friction of the sample.

According to another embodiment of this invention, the rotation device includes a first servomotor and the motion device includes a second servomotor.

According to another embodiment of this invention, the force measurement device comprises a force/torque sensor system.

According to yet another embodiment of this invention, a method of determining the coefficient of friction of a sample, includes the steps of: (a) providing a friction test machine having a curvilinear friction surface, a sample holder and a force measurement device; (b) placing the sample onto the sample holder; (c) adjusting the sample and the curvilinear friction surface into frictional engagement; (d) rotating the curvilinear friction surface; and, (e) using the force measurement device to obtain a measurement indicative of the coefficient of friction of the sample.

According to another embodiment of this invention, the sample is moved vertically into frictional engagement with the curvilinear friction surface.

According to another embodiment of this invention, when the sample and the curvilinear friction surface are adjusted into frictional engagement, a curvilinear deformation is formed in the sample.

According to still another embodiment of this invention, the outer surface of a wheel defines the curvilinear friction surface and, the wheel is rotated a given length of curvilinear surface (between 1 and 3 inches in general) to determine the coefficient of friction.

One advantage of this invention is that very small samples can be used with the friction test machine. One result is that existing tire treads having heavy blading designs can still be sampled.

Another advantage of this invention is that sample edge effects are eliminated and the coefficient of friction can be determined independent of sample geometry.

Another advantage of this invention is that coefficient of friction can be determined independent of traction measurements.

Still another advantage of this invention is that the coefficient of friction of competitor products can be determined even when the specific composition of the product is not known.

Yet other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein:

FIG. 15A is a graph showing the static coefficient of friction results for test compound B (high modulus) versus the test wheel rotational speed and the contact pressure.

IV. DETAILED DESCRIPTION OF THE INVENTION

Figure 1:
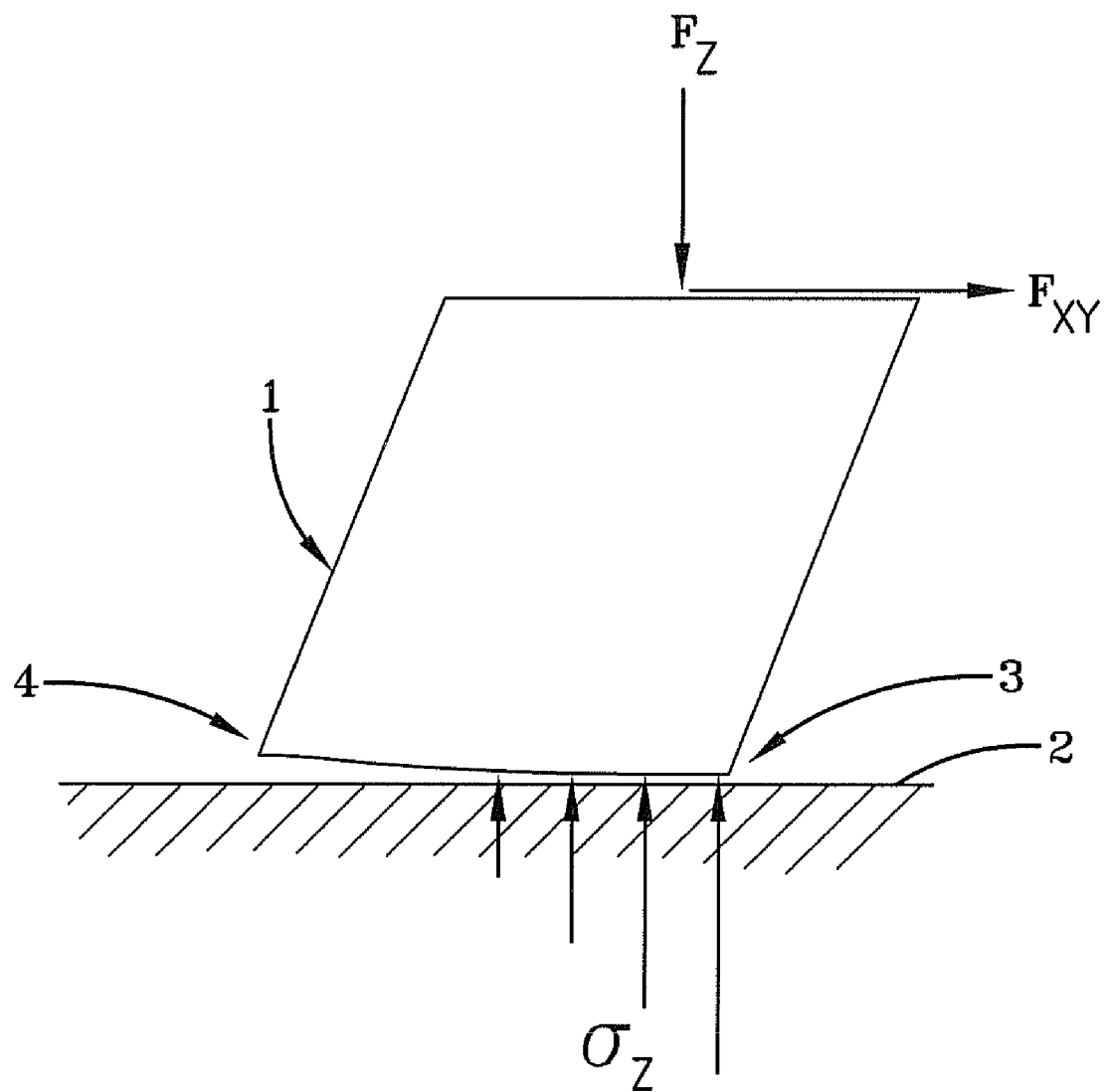
FIG. 1 is an illustration showing how edge effects can distort the true friction characteristics of a sample.
Figure 2:
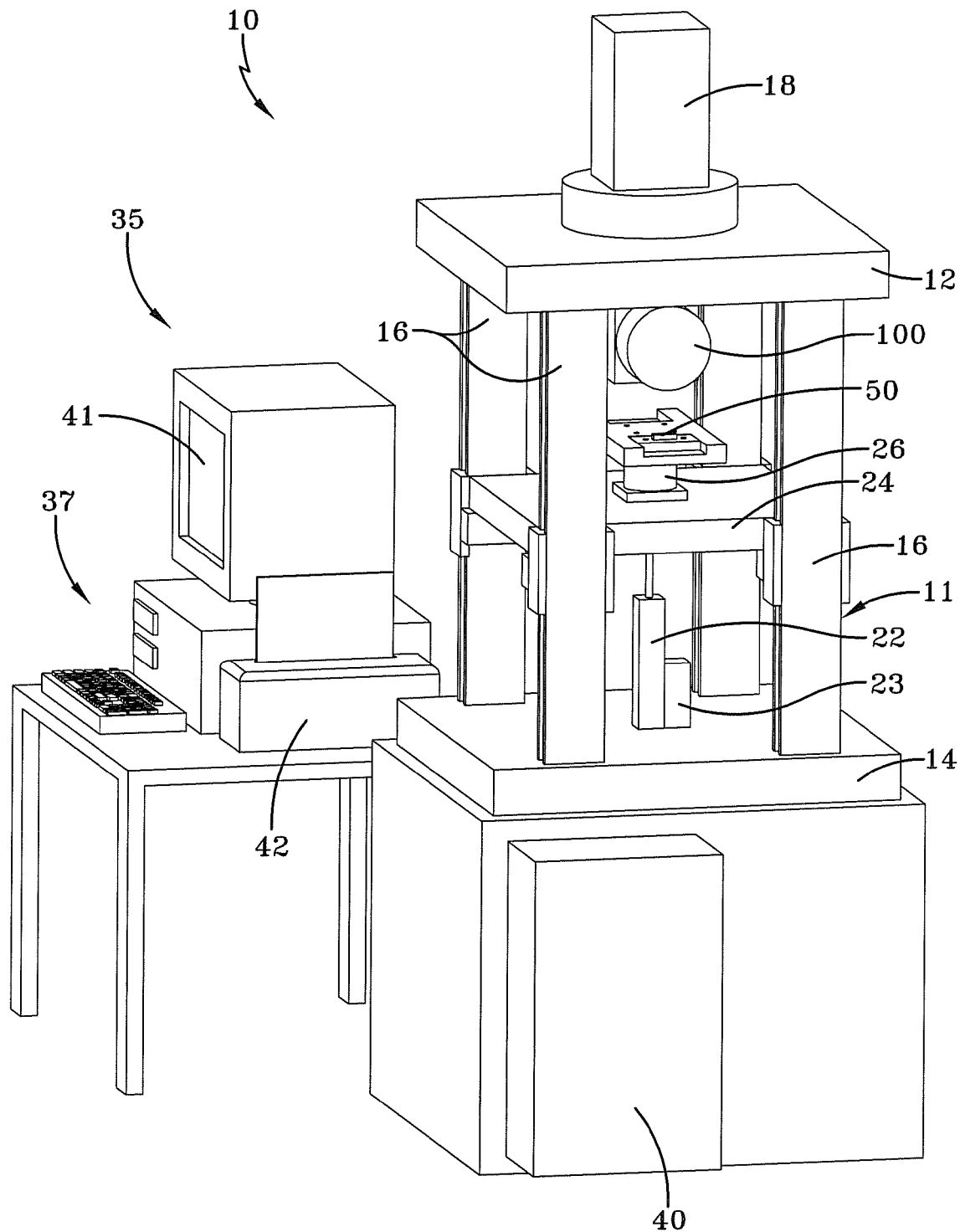
FIG. 2 is a perspective side view of a friction test machine according to one embodiment of this invention.
Figure 3:
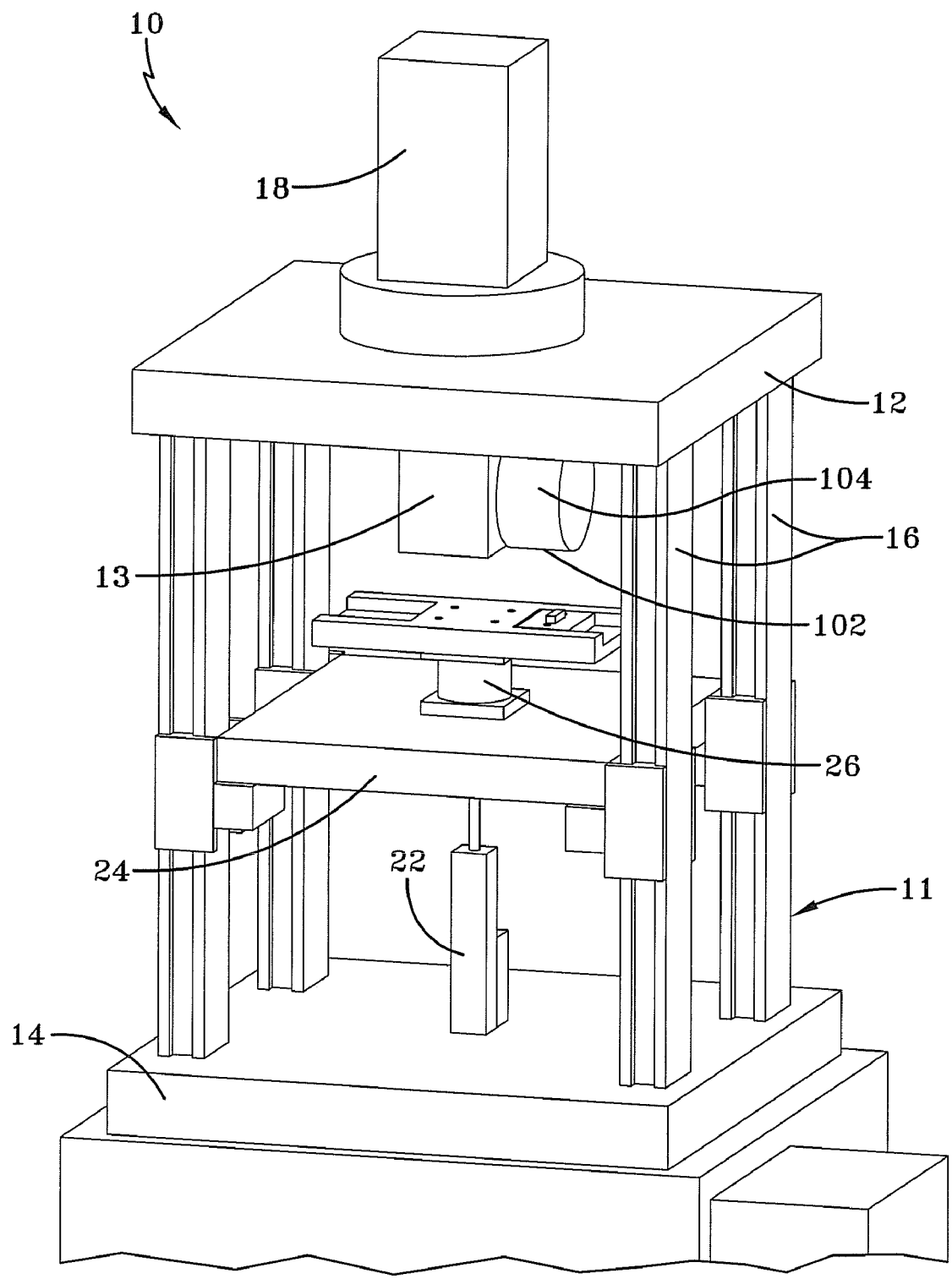
FIG. 3 is a perspective front view of the friction test machine shown in FIG. 2.
Figure 4:
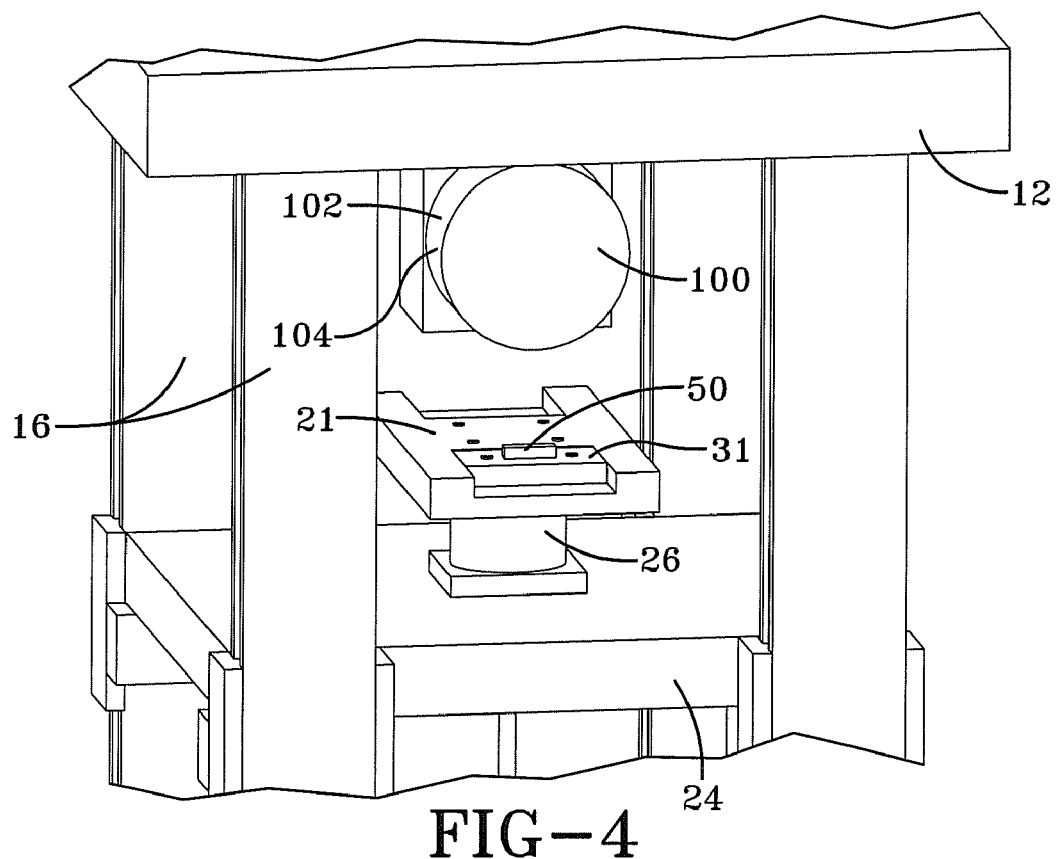
FIG. 4 is a close up view of the friction test machine shown in FIG. 2 showing the wheel defining the curvilinear friction surface.
Figure 5:
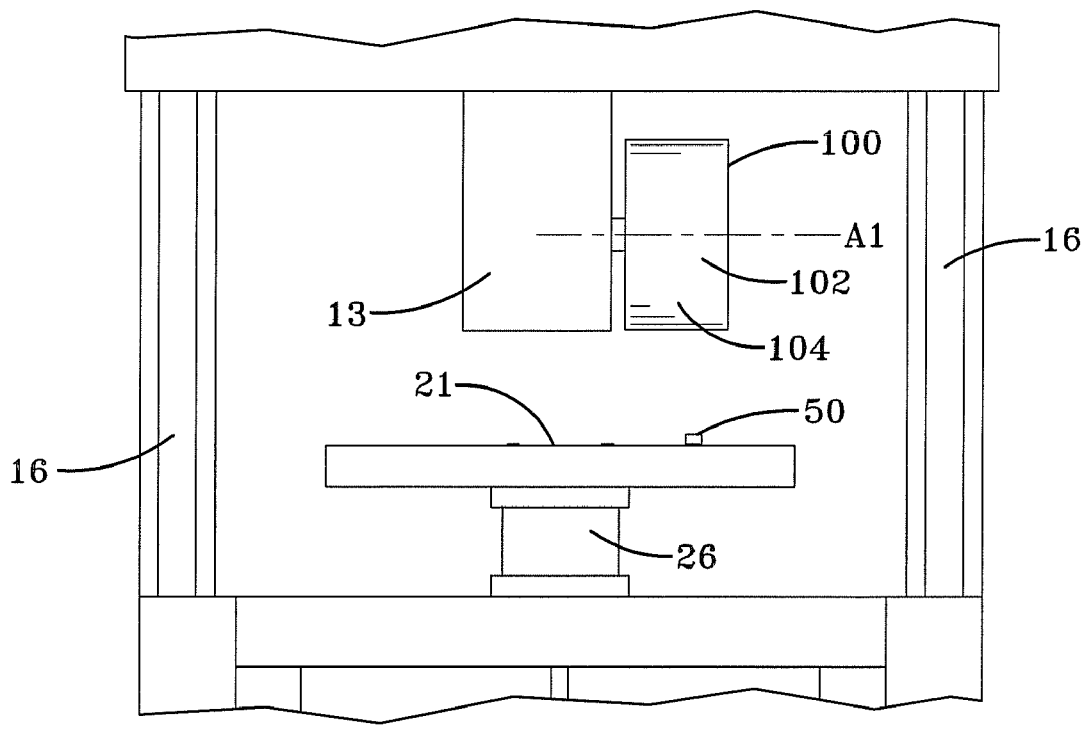
FIG. 5 is a close up view of the friction test machine shown in FIG. 2 showing a front view of the curvilinear friction surface.
Figure 8A:
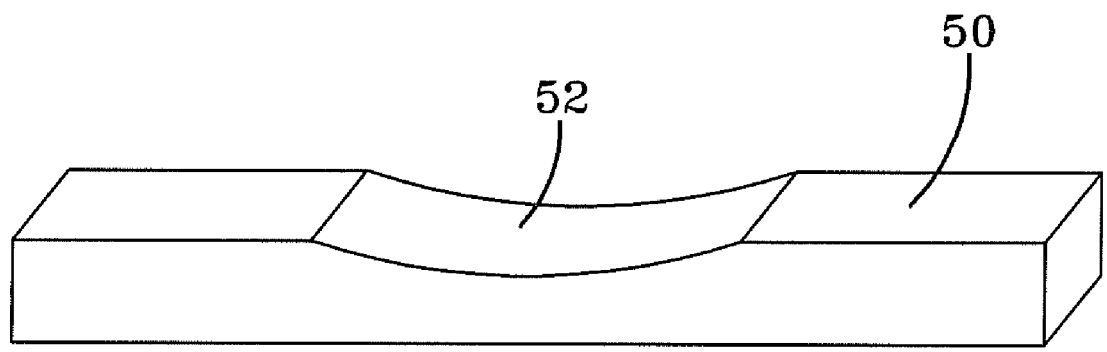
FIG. 8A is a perspective side view of a sample under frictional engagement with a curvilinear friction surface where the curvilinear friction surface has been removed.
Figure 8B:
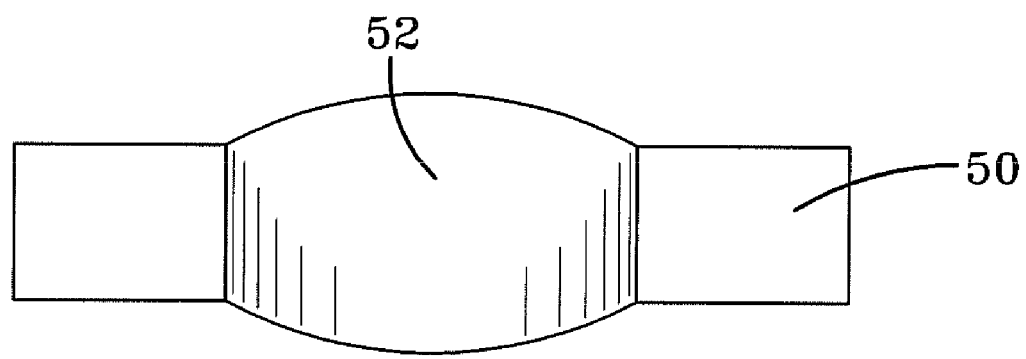
FIG. 8B is a top view of the sample shown in FIG. 7A.

Referring now to the drawings wherein the showings are for purposes of illustrating various embodiments of the invention only and not for purposes of limiting the same, FIGS. 2-4 show a friction test machine 10 that may be used to determine the coefficient of friction (COF) of a sample 50. The friction test machine 10 may include a wheel 100 having an outer surface 102 defining a curvilinear friction surface 104. To determine the COF of the sample 50, the sample 50 and the curvilinear friction surface 104 are adjusted into frictional engagement. This frictional engagement forms a curvilinear deformation 52 in the sample 50 as shown in FIGS. 8A and 8B. The use of the curvilinear friction surface 104 to form the curvilinear deformation 52 enables the friction test machine 10 to eliminate sample edge effects and thus determine the COF independent of sample geometry. This independence from sample geometry means the friction test machine 10 may be used to accurately determine the COF of samples from already existing products, such as an actual tire tread sample. As a result, it is no longer necessary to make samples in order to determine the COF. This means that the COF of competitor products can easily and accurately be determined even when the specific composition of the product is not known.

Figure 9:
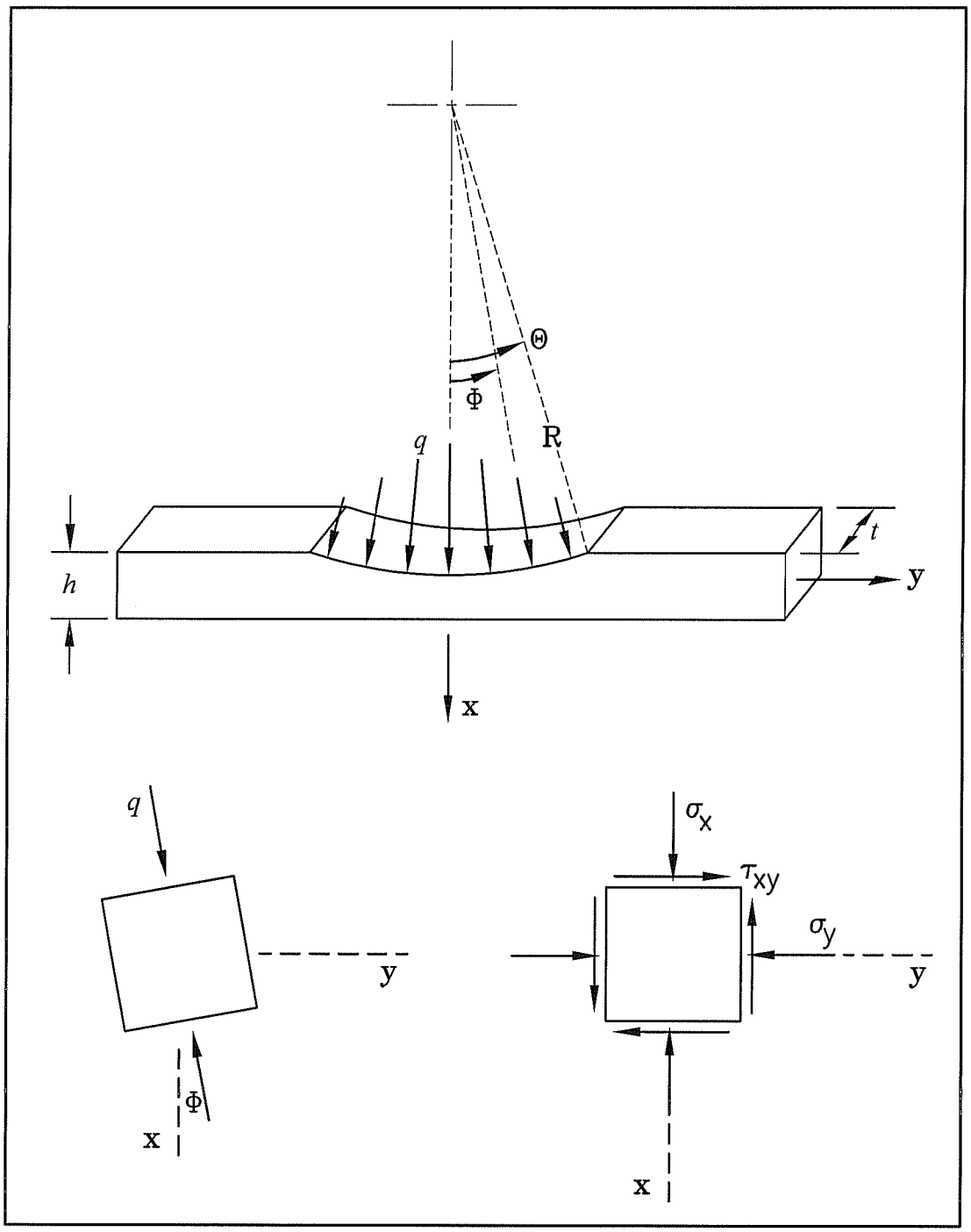
FIG. 9 illustrates plane stress transformation images used to determine the stress contact surface.

Prior to further discussion of the friction test machine a theoretical analysis will be provided. With reference now to FIG. 9, based on plane stress assumption & stress transformation as shown, the stresses on the contact surface can be expressed as $$\sigma_x = q\cos^2(\phi),\ \sigma_y = q\sin^2(\phi),\ \tau_{xy} = q\sin(\phi)\cos(\phi)$$

$$\sigma_z = \tau_{yz} = \tau_{zx} = 0 \tag{A1}$$

where $-\theta < \phi < \theta$ and q is the contact pressure

Therefore, the strain components can be expressed as $$\varepsilon_x = \frac{1}{E}(\sigma_x - \nu\sigma_y), \tag{A2}$$

$$\varepsilon_y = \frac{1}{E}(\sigma_y - \nu\sigma_x),$$

$$\varepsilon_z = \frac{-\nu}{E}(\sigma_x + \sigma_y) = -\frac{\nu}{E}q$$

$$\gamma_{xy} = G\tau_{xy},$$

$$\gamma_{yz} = \gamma_{zx} = 0$$

As a rigid wheel with radius R compressed on the rubber sample, the deformation in x-direction of a point on the contact surface at angle ϕ should be $$d = R[\cos(\phi) - \cos(\theta)],$$

the maximum deformation at ϕ=0 is $$d_o = R[1 - \cos(\theta)] \tag{A3}$$

Due to rigid wheel compressed, the $\varepsilon_x$ at contact surface at angle ϕ can be simply expressed as $$\varepsilon_x = -\frac{d}{h} = -\frac{R}{h}[\cos(\phi) - \cos(\theta)], \quad (A4)$$

where h is the thickness of the rubber sample

Combining the Eqs. (A1), (A2) and (A4), the contact pressure q can be obtained as $$q = -\frac{ER}{h}\frac{\cos(\phi) - \cos(\theta)}{\cos^2(\phi) - v\sin^2(\phi)} \quad (A5)$$

Substituting Eq. (A5) into Eq. (A1) yields $$\sigma_x = -\frac{ER}{h}\frac{\cos(\phi) - \cos(\theta)}{\cos^2(\phi) - v\sin^2(\phi)}\cos^2(\phi) \quad (A6)$$

$$\sigma_y = -\frac{ER}{h}\frac{\cos(\phi) - \cos(\theta)}{\cos^2(\phi) - v\sin^2(\phi)}\sin^2(\phi)$$

The total force applied on the contact area is $$F_x = \int_{-\theta}^{\theta} \sigma_x (1+\varepsilon_z) tR\cos(\phi) d\phi \quad (A7)$$

$$= -\frac{EtR^2}{h} \int_{-\theta}^{\theta} \frac{(\cos(\phi) - \cos(\theta))\cos^3(\phi)}{\cos^2(\phi) - v\sin^2(\phi)}$$

$$\left(1 + \frac{vR}{h}\frac{\cos(\phi) - \cos(\theta)}{\cos^2(\phi) - v\sin^2(\phi)}\right) d\phi$$

$$F_y = \int_{-\theta}^{\theta} \sigma_y (1+\varepsilon_z) tR\sin(\phi) d\phi = 0$$

where t is the width of the sample

Due to Poisson's effect, the sample width at angle o on the contact surface is $(1+\varepsilon_z)t$. Therefore, the affective area of the normal force $F_x$ is $$A_x = \int (1+\varepsilon_z) t dy \quad (A8)$$

$$= tR \int_{-\theta}^{\theta} \left(1 + \frac{vR}{h}\frac{\cos(\phi) - \cos(\theta)}{\cos^2(\phi) - v\sin^2(\phi)}\right)\cos(\phi) d\phi$$

The average contact pressure can be expressed as $$P_{avg} = \left|\frac{F_x}{A_x}\right| \quad (A9)$$

$$= \frac{ER}{h} \frac{\int_{-\theta}^{\theta} \frac{(\cos(\phi) - \cos(\theta))\cos^3(\phi)}{\cos^2(\phi) - v\sin^2(\phi)} \left(1 + \frac{vR}{h}\frac{\cos(\phi) - \cos(\theta)}{\cos^2(\phi) - v\sin^2(\phi)}\right) d\phi}{\int_{-\theta}^{\theta} \left(1 + \frac{vR}{h}\frac{\cos(\phi) - \cos(\theta)}{\cos^2(\phi) - v\sin^2(\phi)}\right)\cos(\phi) d\phi}$$

II. How to Determine the Average Contact Pressure

As shown in Eqs. (A7)-(A9), the integration in the formula can not be solved directly. Numerical integration method was used to obtain the values at each sample size and contact angle. However, there is no way to obtain the accurate contact angle θ in the experimental process. Normally, the total normal force ($F_x$) and the reaction friction force (fμ) are able to be measured accurately in the experimental process. The maximum deformation ($d_o$) of the rubber sample may include an offset value in the measurement due to the difficulty of the determination of zero position at the beginning of contact.

Therefore, there is a requirement to simplify the process and formula for testing condition determination. First, the Eqs. (A8) can be approximated as $$A_x = \int (1+\varepsilon_z)t dy \quad (A10)$$

$$\approx tR \int_{\theta}^{\theta} \left(1 + \frac{vR}{h}[\cos(\phi) - \cos(\theta)]\right)\cos(\phi) d\phi$$

$$\approx tR\left[2\sin(\theta) + \frac{vR}{h}\left(\theta - \frac{\sin(2\theta)}{2}\right)\right]$$

When angle θ is small.

Figure 10:
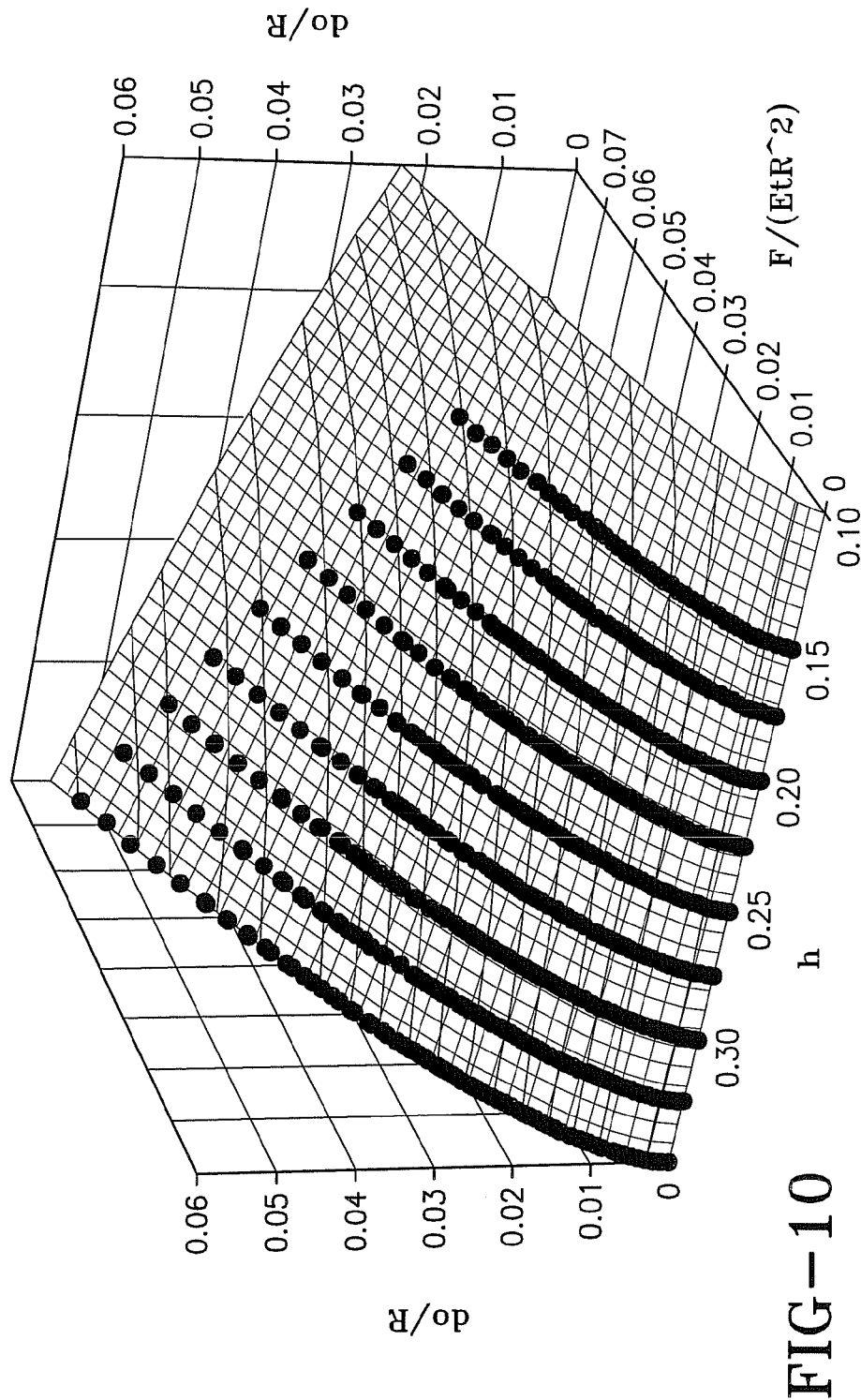
FIG. 10 is a contact area comparison between equation A8 and equation A10.
Figure 11:
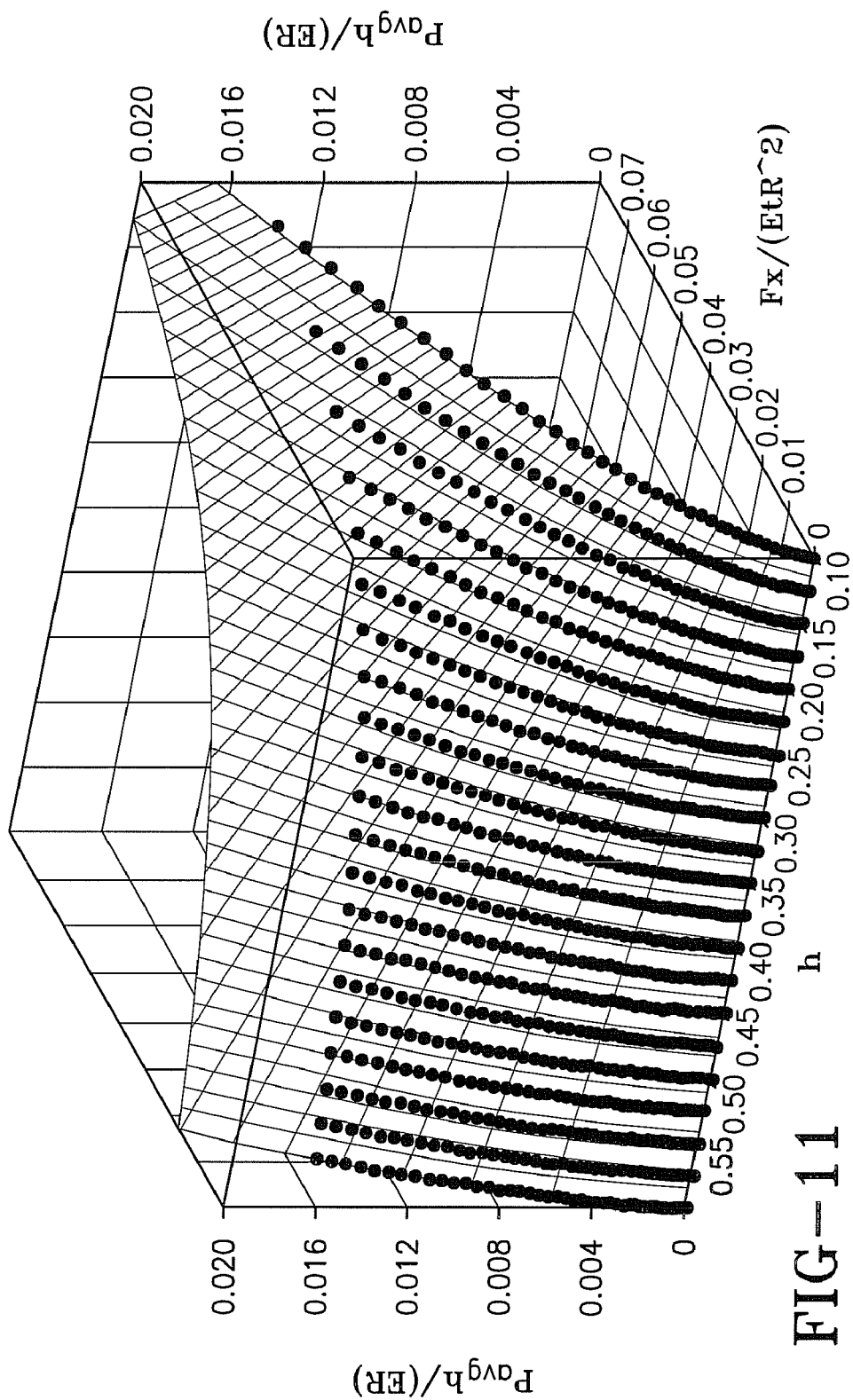
FIG. 11 is a contact area verification using ink footprint measurement.

As shown in FIGS. 9 and 10, the contact area approximation was verified by numerical and experimental comparisons.

Therefore, the average contact pressure was expressed as $$P_{avg} = \left|\frac{F_x}{A_x}\right| \quad (A11)$$

$$\approx \frac{|F_x|}{tR\left[2\sin(\theta) + \frac{vR}{h}\left(\theta - \frac{\sin(2\theta)}{2}\right)\right]}$$

As shown in Eq. (A11), there is only one undetermined variable θ. The $F_x$ can be experimentally measured through the process, the t and h are the sample dimensions and R is the radius of the curvilinear surface.

According to contact theory between flat soft material and rigid curvilinear surface, the maximum deformation ($d_o$) as shown in FIG. 8 can be expressed as simple power function of applied normal force ($F_x$). Normally, an offset value Δ is included in the experimentally obtained maximum deformation $d'_o$.

$$d_o = d'_o - \Delta = kF_x^b$$

$$d'_o = kF_x^b + \Delta \quad (A12)$$

The k, b and Δ in Eq. (A12) can be easily determined by a simple load deflection test and numerical regression method. Combining Eqs. (A3) and (A12), the contact angle θ of a given normal load $F_{xg}$ can be easily obtained $$\theta = \cos^{-1}\left(1 - \frac{kF_{xg}^b}{R}\right) \quad (A13)$$

Substituting Eq. (A13) into Eqs. (A10) and (A11) yields the contact area and average contact pressure of a given normal load $F_{xg}$.

The coefficient of friction can be calculated based on the definition of the coefficient of friction of uniform load distribution $$\mu = \frac{f}{F} \quad (A21)$$

c change to (A14)

where F is the normal load and f is the friction force.

As we know, the coefficient of friction of tread compound is highly dependant on the contact pressure. Therefore, the coefficient of friction in this case need to be determined by $$\mu_{avg} = \frac{\int \mu(q) q \, dA}{\int q \, dA} = \frac{\int \mu(q) q \, dA}{F} \quad (A22)$$

change to (A15)

where q is the contact pressure and $\mu(q)$ is the coefficient of friction at contact pressure q.

With reference now to FIGS. 2-7, the construction and use of the friction test machine 10 will now be described. The friction test machine 10 may have a frame 11 used to support the wheel 100 and the sample 50. While the frame 11 can have any design chosen with sound engineering judgment, for the embodiment shown the frame 11 comprises a base plate 14, and vertical guide bars 16 extending generally upward from the base plate 14. The friction test machine 10 may also include a top plate 12 attached to the top portions of the vertical guide bars 16. The previously noted wheel 100 may be attached to the top plate 12 via gearbox 13, as shown. A servomotor 18 may be mounted to the top 12 with its drive shaft oriented vertically downward and received with the gearbox 13. The wheel 100, when activated by the servomotor 18, rotates about horizontal axis A1, shown in FIG. 5. A sample mount 21 is configured to hold a sample 50. The sample mount 21 is supported on movable plate 24 which engages the vertical guide bars 16 and is slidable thereon. A loading cylinder or actuator 22 may be positioned beneath the plate 24 and used to move the plate 24 along the guide bars 16 to thereby adjust the sample 50 into frictional engagement with the curvilinear friction surface 104. A servomotor 23 may be mounted to the base plate 14 and used to power the actuator 22 in a known manner. A loading cell 26 configures to measure both load and torque may be mounted between the plate 24 and the sample mount 21, as shown.

Figure 6:
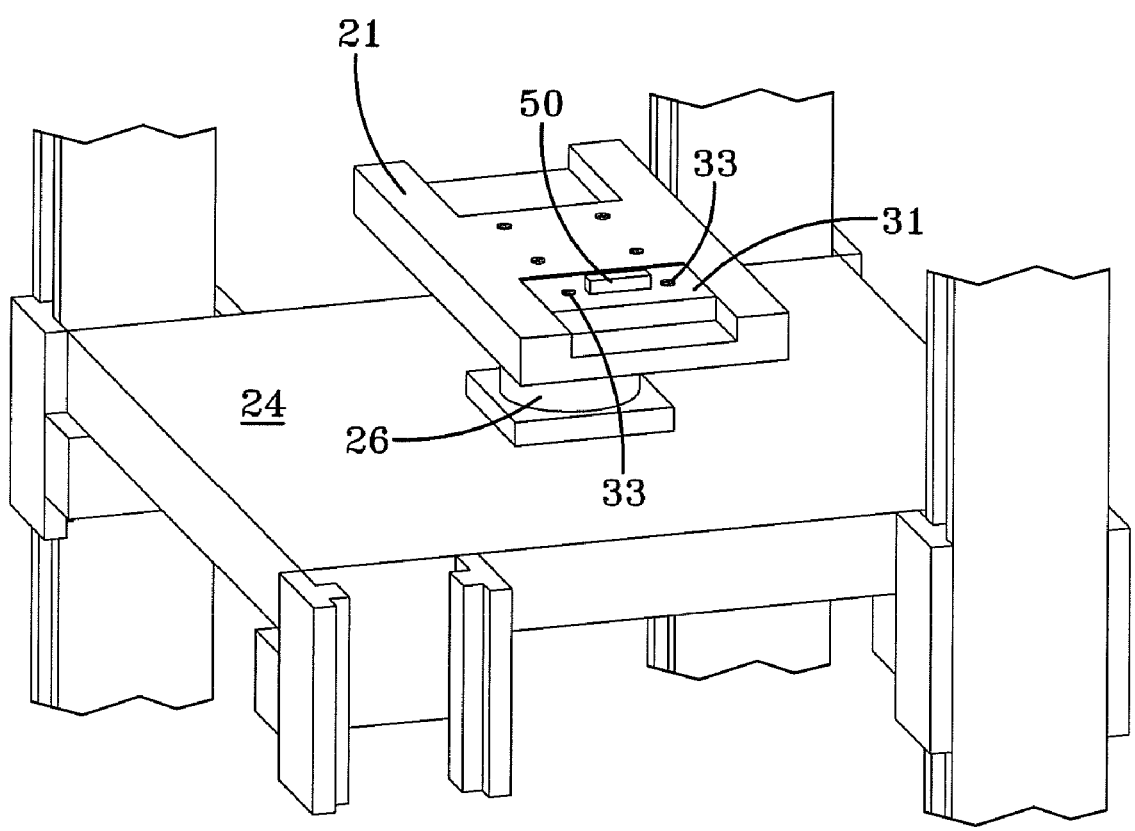
FIG. 6 is a close up view of a portion of the friction test machine of FIG. 2 showing the sample holder holding a sample.
Figure 7:
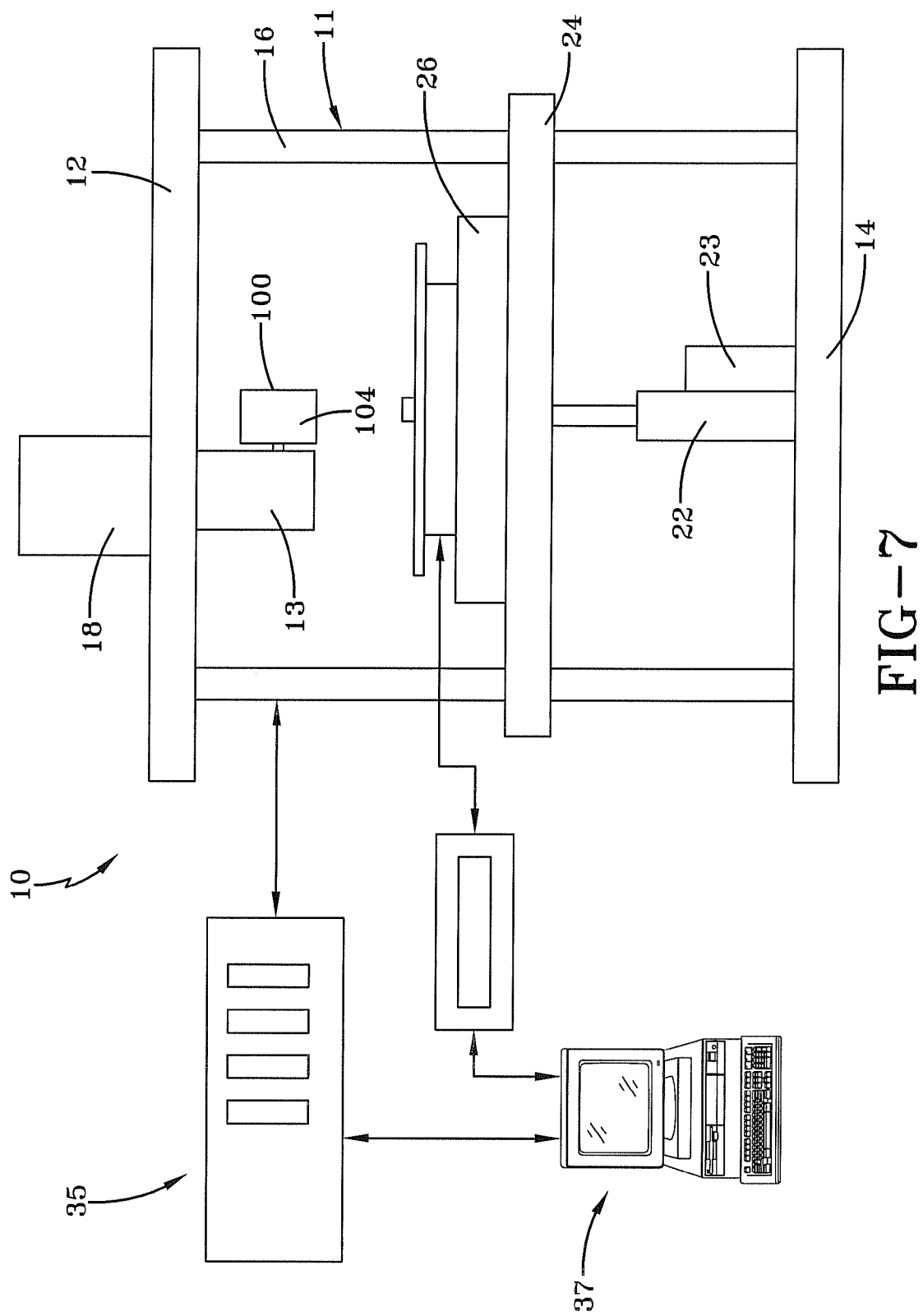
FIG. 7 is a schematic representation of the friction test machine.

With reference now to FIGS. 4 and 6, a sample 50 may be attached to a sample holder 31 which can then be attached to the sample mount 21 by any means chosen with sound engineering judgment such as with the use of screws 33 as shown. It may be advantageous to use an adhesive to hold the sample 50 to the sample holder 31. It should be noted that this invention permits the use of very small samples. Thus, for instance, the sample may be on the order of 1" in length by ¼" in width by ¼" in height. However, it should be noted that both larger and smaller samples may be used with this invention.

With reference again to FIGS. 2-7, the previously described servomotors 18, 23 and loading cell 26 may be connected to a controller 35 and data acquisition system 37 chosen with sound engineering judgment. The controller 35 may include, for example, a control panel 40, a computer 41, and a printer 42. The control panel 40 may be used to manually control the contact pressure between the sample 50 and the wheel 100 and to control the speed of rotation of the wheel 100. Alternatively, the computer 41 may be used to program these parameters to provide a specific sequence of parameter changes. In one embodiment, the computer 41 may be used as the data acquisition system 37 and motion control station by using typical off-the-shelf PC based motion control and data acquisition boards. The data acquisition system was used to collect the force data (normal force and friction force) and provide feedback information to the motion control station through the friction test.

With reference now to FIGS. 4, 7, 8A and 8B, the contact surface between the sample 50 and the curvilinear friction surface 104 will now be discussed. First, as noted above, the curvilinear friction surface 104 forms a curvilinear deformation 52 in the sample 50 (shown in FIGS. 8A and 8B). This curvilinear contact surface eliminates edge effects and thus provides geometry independent values of the COF. The friction test machine 10 measures pointwise values of the COF as a function of contact pressure, speed of rotation of the wheel 100, ambient temperature, and outer surface 102 characteristics. This data can be used in predictive tire models, such as rolling three dimensional (3-D) finite element models, which account for the geometric contributions of tire design to traction. The curvilinear contact surface makes it possible to calculate an analytical contact area so that precise calculation of average contact pressure can be made. The theoretical basis for this has been described above.

With reference to FIGS. 2-8B, the basic operation of the friction test machine 10 will now be described. First, the sample 50 is placed onto the sample holder 31 which is then placed onto the sample mount 21. As noted above, it may be desirable to use an adhesive to hold the sample 50 to the sample holder 31. The specific sample used with the friction test machine 10 can be of any composition that, under load with the curvilinear friction surface 104, compresses into a corresponding curvilinear deformation 52. Samples formed of elastomeric materials, for a non-limiting example, are thus well suited for use with the friction test machine 10. Tire components and athletic shoe components are two specific examples that work well with this invention. Because of the elimination of edge effects, the sample can be taken from a pre-existing product, such as an existing tire tread.

With continuing reference to FIGS. 2-8B, once the sample 50 is mounted, the sample 50 and the curvilinear friction surface 104 are adjusted into frictional engagement. This may be accomplished by operating the servo motor 23 to operate the actuator 22 to move the plate 24 (and thus the sample 50) vertically upward along the guide bars 16. The loading cell 26 can be used to confirm that the appropriate load has been achieved. The wheel 100 and thus the curvilinear friction surface 104 is then rotated with respect to the sample 50 and the loading cell 26 measures the load and torque. These measurements are then transferred to the data acquisition system 37 where the COF can be accurately determined. In one embodiment, these measurements are indicative of both static and kinetic COF of the sample 50. It should be noted that the amount of rotation of the wheel 100 required to obtain accurate measurements is very small. In one embodiment, the wheel need only by rotated less than 10 degrees. In another embodiment the wheel may be rotated less than 5 degrees and in yet another embodiment the wheel may be rotated less than 2 degrees.

Figure 12:
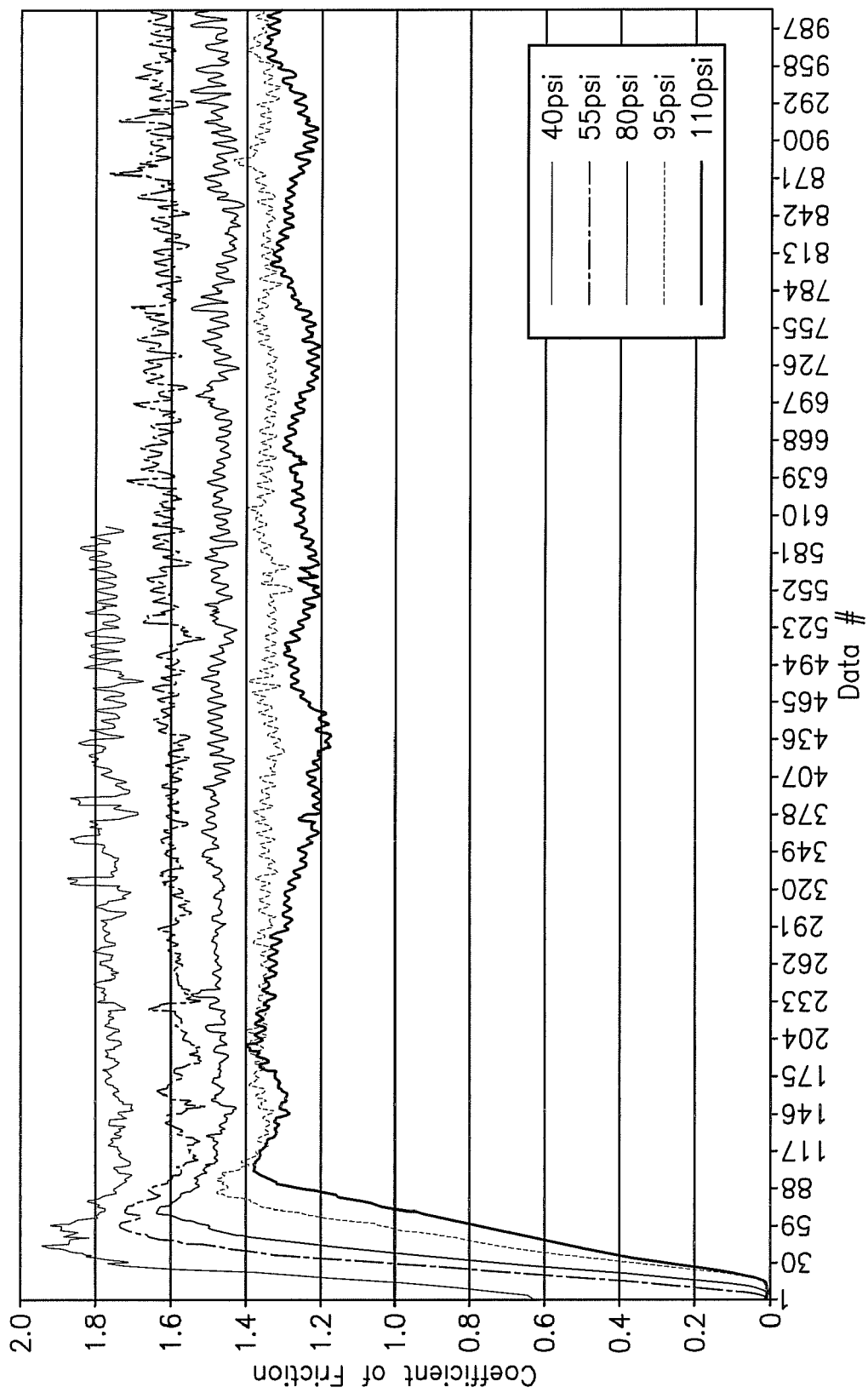
FIG. 12 shows coefficient of friction curves for a sample tested on the friction test machine of this invention.

FIG. 12 shows examples of COF results using the friction test machine 10 at five different average contact pressures, measured in pounds per square inch (psi) with the wheel curvilinear surface rotated at 1.245 inches per second on a typical passenger tire tread compound.

Figure 13:
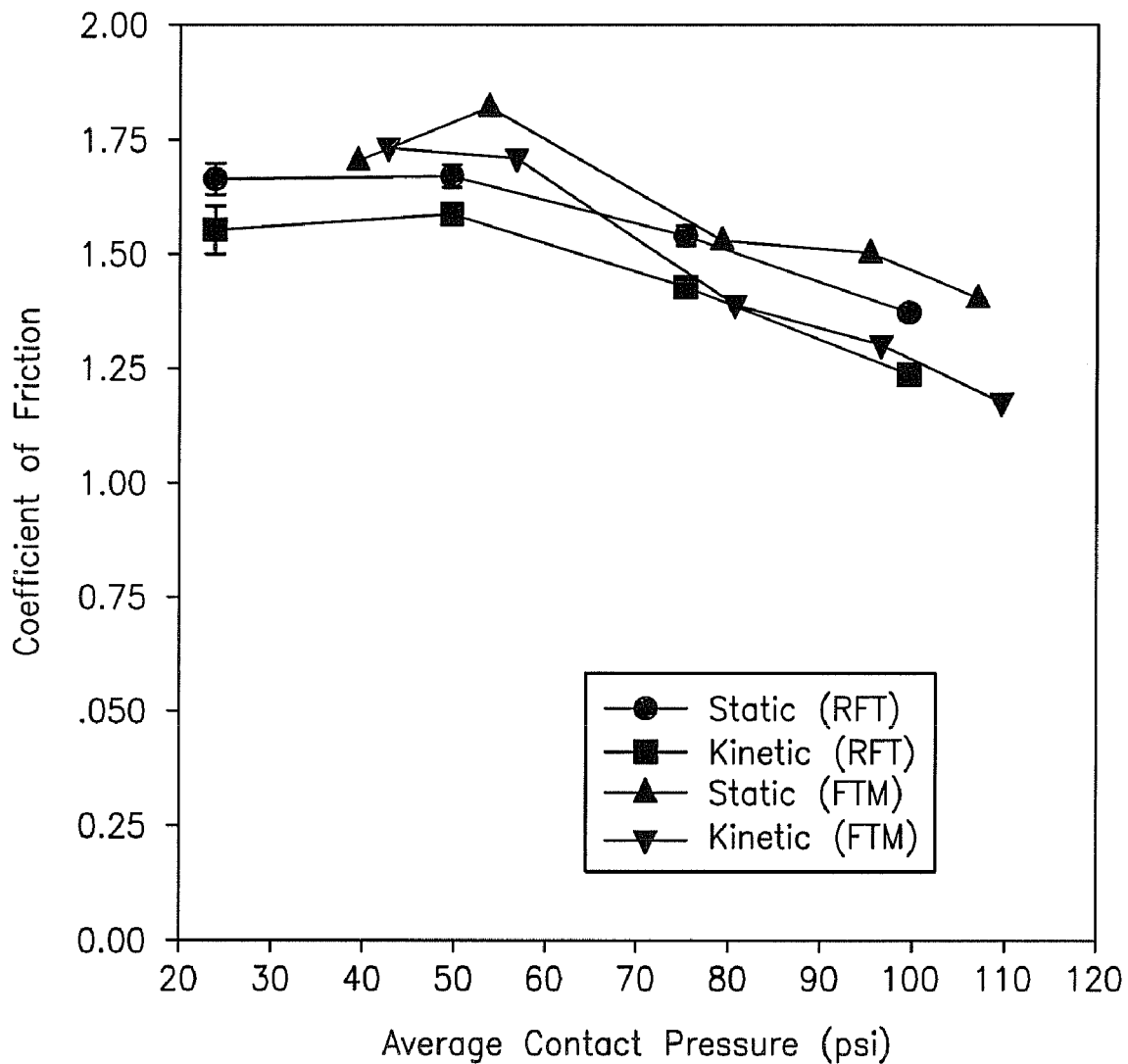
FIG. 13 shows a comparison between coefficient of friction results determined using the friction test machine of this invention and those determined using applicant's earlier invention on a control compound.
Figure 14A:
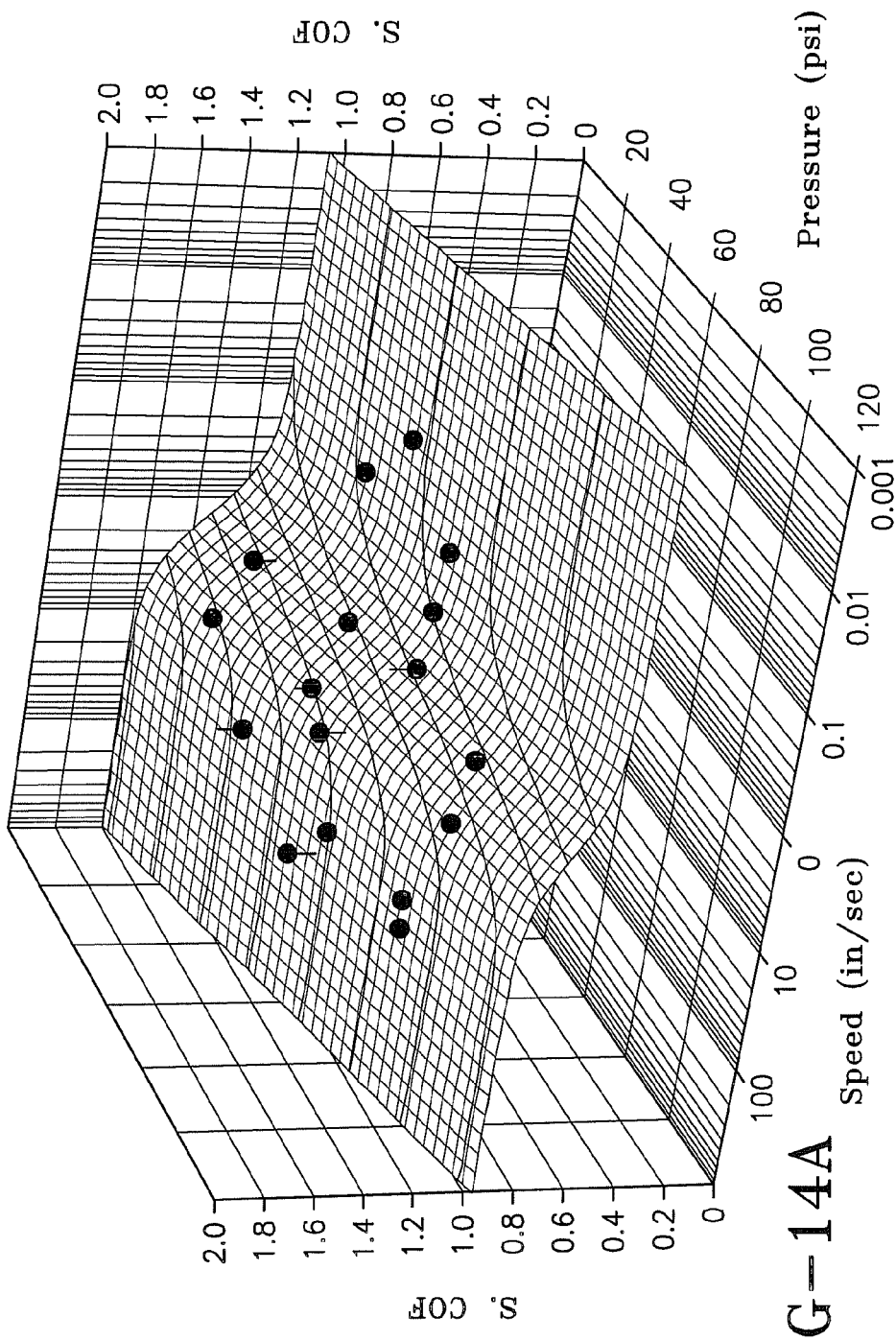
FIG. 14A is a graph showing the static coefficient of friction results for test compound A (low modulus) versus the test wheel rotational speed and the contact pressure.
Figure 14B:
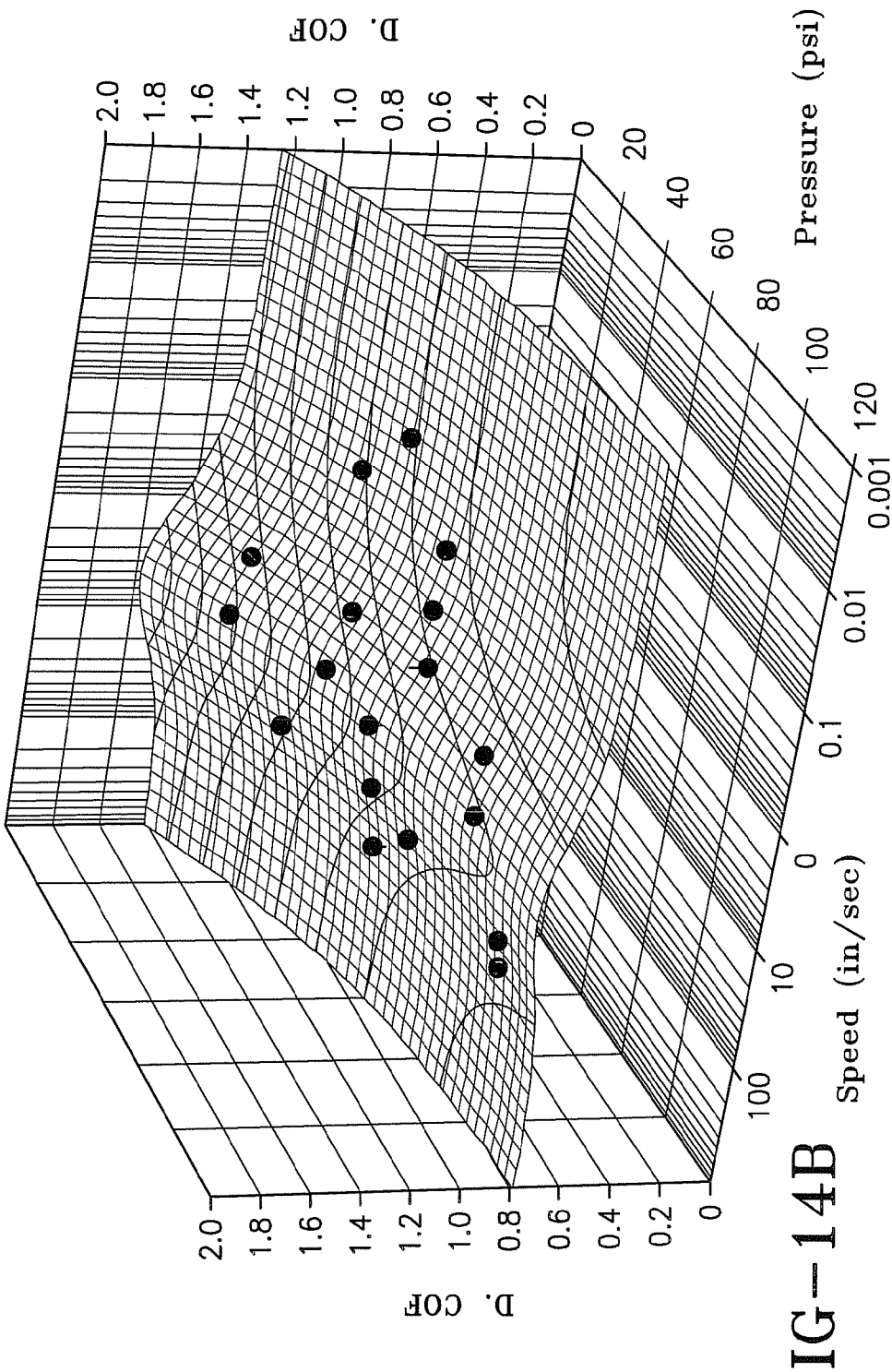
FIG. 14B is a graph showing the dynamic coefficient of friction results for test compound A (low modulus) versus the test wheel rotational speed and the contact pressure.
Figure 15B:
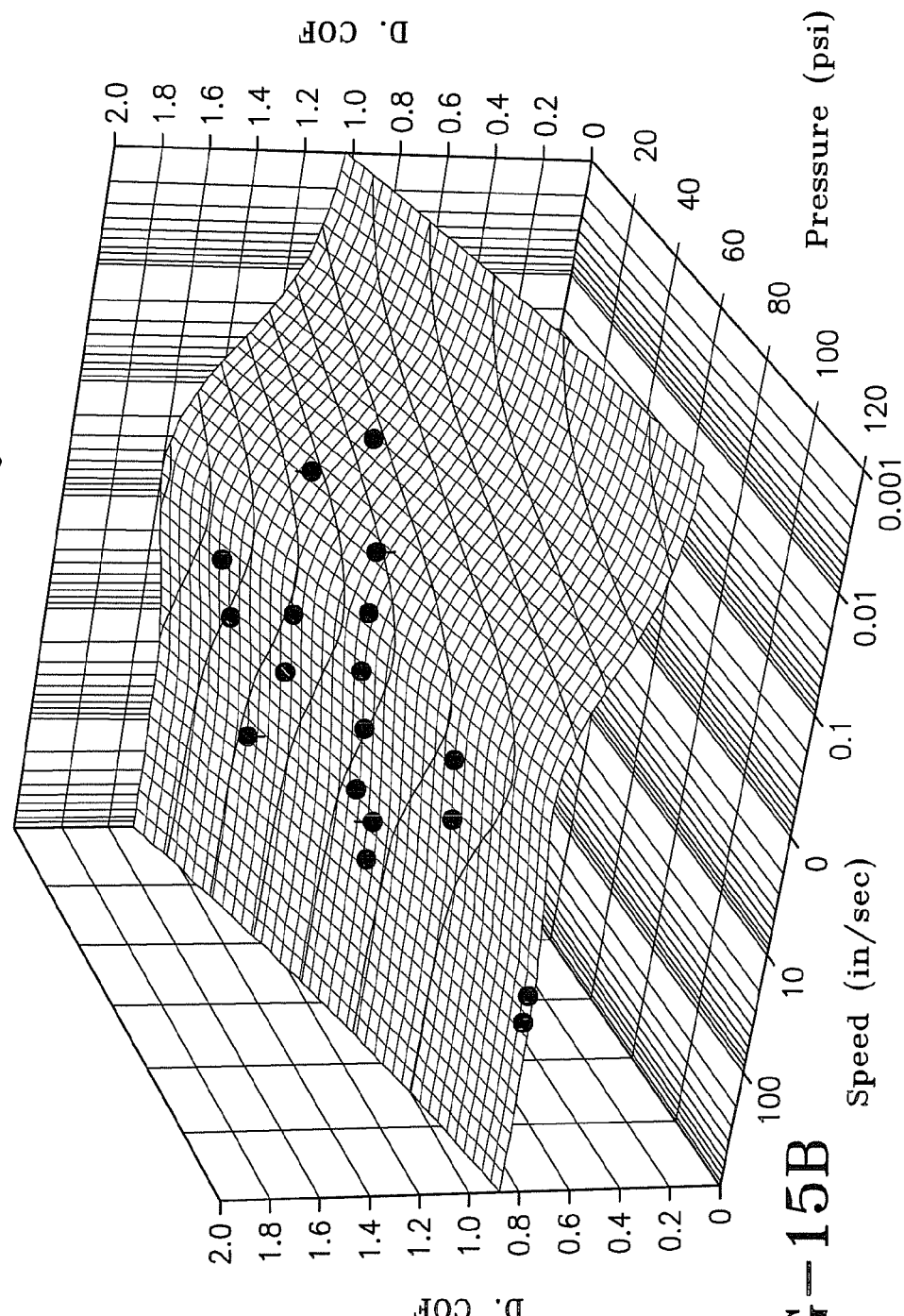
FIG. 15B is a graph showing the dynamic coefficient of friction results for test compound B (high modulus) versus the test wheel rotational speed and the contact pressure.

FIG. 13 shows a comparison of COF data determined using the friction test machine 10 of this invention, labeled FTM, and determined using the Rotational Friction Tester (RFT) described above. As FIG. 13 indicates, the results correlate very well both for static and kinetic COF values.

With reference now to FIGS. 14A-15B, the friction test machine 10 (FTM) was used in a trial with 2 rubber compounds labeled A-B directly cut from tires. The two tire tread compounds had significant difference on modulus indicated as low and high respectively. Coefficient of friction was tested under a wide range of speeds and pressures. The speed indicates the steady state curvilinear surface speed. As shown in FIGS. 14A-15B, the differences in coefficient of friction for these two compounds were clearly measured by the friction test machine 10.

Embodiments of the invention have been described, hereinabove. It will be apparent to those skilled in the art that the above methods and apparatus may incorporate changes and modifications without departing from the general scope of this invention. It is intended to include all such modifications and alterations in so far as they come within the scope of the appended claims or the equivalents thereof. For example, those skilled in the art will recognize that other arrangements of apparatus 10 may be possible without changing its operation. The loading cylinder or actuator 22, for instance, could be replaced with other loading means. The load between the test wheel and the specimen could be applied by a pneumatic cylinder, a hydraulic cylinder, a servomotor, a linear actuator, a screw jack, or a dead weight and pulley system, just to name a few alternate methods. Also the vertical movement of the plate 24 (and thus the sample 50) and the horizontal axis A1 of the wheel could be altered to any other direction chosen with sound engineering judgment. Similarly, the positions of the servo motors 18, 23 and the load cell 26 could be changed. Rotation of the wheel could be accomplished by a servomotor, an electric motor and gearbox, a hydraulic torque motor or any other means to apply rotation to the wheel. The wheel itself can be made of any material or any combination of materials. For example, it could be made of any metal, have asphalt or concrete inserts, be covered with an abrasive material. The wheel may also have any topography that could be of interest.

The invention claimed is:

1. A friction test machine comprising:
   a frame;
   a curvilinear friction surface;
   a rotation device operatively connected to the frame and configured to selectively rotate the curvilinear friction surface;
   a sample holder configured to hold an associated sample;
   a motion device operatively connected to the frame and configured to selectively adjust the associated sample and the curvilinear friction surface into frictional engagement, such that a curvilinear deformation is formed in the associated sample; and,
   a force measurement device for obtaining a measurement indicative of the coefficient of friction of the sample.

2. The friction test machine of claim 1 wherein the outer surface of a wheel defines the curvilinear friction surface and the rotation device is configured to selectively rotate the wheel.

3. The friction test machine of claim 1 wherein the force measurement device is configured to obtain a measurement indicative of the coefficient of friction of an elastomeric sample.

4. The friction test machine of claim 3 wherein the force measurement device is configured to obtain a measurement indicative of the coefficient of friction of an actual tire tread sample.

5. The friction test machine of claim 1 herein the force measurement device is configured to obtain a measurement indicative of the coefficient of friction of a sample having a size as small as 0.25 inches by 0.25 inches by 1.0 inches.

6. The friction test machine of claim 1 wherein the force measurement device is configured to obtain a measurement indicative of both static and kinetic coefficient of friction of the sample.

7. The friction test machine of claim 1 wherein:
   the rotation device comprises a first servomotor; and,
   the motion device comprises a second servomotor.

8. The friction test machine of claim 1 wherein the force measurement device comprises a force/torque sensor system.

9. A method of determining the coefficient of friction of a sample, comprising the steps of:
   providing a friction test machine comprising: (a) a curvilinear friction surface; (b) a sample holder; and, (c) a force measurement device;
   placing the sample onto the sample holder;
   adjusting the sample and the curvilinear friction surface into frictional engagement and forming a curvilinear deformation in the sample;
   rotating the curvilinear friction surface; and,
   using the force measurement device to obtain a measurement indicative of the coefficient of friction of the sample.

10. The method of claim 9 wherein:
    the step of, adjusting the sample and the curvilinear friction surface into frictional engagement, comprises the step of moving the sample in a substantially vertical direction; and,
    the step of, rotating the curvilinear friction surface, comprises the step of rotating the curvilinear friction surface about a substantially horizontal axis.

11. The method of claim 9 wherein:
    the step of, providing a curvilinear friction surface, comprises the step of providing a wheel where the outer surface of the wheel defines the curvilinear friction surface; and,
    the step of rotating the curvilinear friction surface, comprises the step of rotating the wheel less than 10 degrees.

12. The method of claim 11 wherein the step of, rotating the wheel less than 10 degrees, comprises the step of rotating the wheel less than 5 degrees.

13. The method of claim 12 wherein the step of, rotating the wheel less than 5 degrees, comprises the step of rotating the wheel less than 2 degrees.

14. The method of claim 9 wherein the step of, using the force measurement device to obtain a measurement indicative of the coefficient of friction of the sample, comprises the step of:
    obtaining a geometry independent measurement indicative of the coefficient of friction of the sample.

15. A method of determining the coefficient of friction of an elastomeric sample, comprising the steps of:
    providing a friction test machine comprising: (a) a rigid wheel having an outer surface defining a curvilinear friction surface; (b) a sample holder; and, (c) a force measurement device;
    placing the elastomeric sample onto the sample holder;
    adjusting the elastomeric sample and the curvilinear friction surface into frictional engagement thereby forming a curvilinear deformation in the elastomeric sample;
    rotating the rigid wheel; and,
    using the force measurement device to obtain a geometry independent measurement indicative of the coefficient of friction of the elastomeric sample.

16. The method of claim 15 wherein the step of, using the force measurement device to obtain a geometry independent measurement indicative of the coefficient of friction of the elastomeric sample, comprises the step of:

obtaining a measurement indicative of both static and kinetic coefficient of friction of the elastomeric sample.

17. The method of claim 15 wherein the step of, placing the elastomeric sample onto the sample holder, comprises the step of:

placing an actual tire tread sample onto the sample holder.

18. The friction test machine of claim 1, wherein the machine further comprises:

a base plate attached to the frame;

vertical guide bars extending upward from the base plate; and, a top plate attached to top portions of the vertical guide bars, wherein the curvilinear friction surface is attached to the top plate via a gearbox.

19. The friction test machine of claim 18, wherein the machine further comprises:

a servomotor, wherein the servomotor has a drive shaft oriented vertically downward and received with the gearbox, wherein the sample mount is supported on a movable plate which engages the vertical guide bars and is slidable thereon;

a loading cylinder positioned beneath the plate to move the plate along the guide bars to thereby adjust the sample into frictional engagement with the curvilinear friction surface; and, a loading cell configured to measure both load and torque, wherein the loading cell is mounted between the plate and the sample mount.

* * * * *